US009943387B2

United States Patent
Fobi et al.

(10) Patent No.: US 9,943,387 B2
(45) Date of Patent: Apr. 17, 2018

(54) UNMANNED AERIAL VEHICLE-BASED SYSTEM FOR LIVESTOCK PARASITE AMELIORATION

(71) Applicant: International Business Machines Corporation, Armonk, NY (US)

(72) Inventors: Simone Fobi, Nairobi (KE); Clifford A. Pickover, Yorktown Heights, NY (US); Komminist Sisai Weldemariam, Nairobi (KE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/197,310

(22) Filed: Jun. 29, 2016

(65) Prior Publication Data
US 2018/0000575 A1    Jan. 4, 2018

(51) Int. Cl.
| G01C 23/00 | (2006.01) |
| A61D 7/00  | (2006.01) |
| B64C 39/02 | (2006.01) |
| A61B 90/00 | (2016.01) |

(52) U.S. Cl.
CPC .............. *A61D 7/00* (2013.01); *A61B 90/36* (2016.02); *B64C 39/024* (2013.01); *B64C 2201/12* (2013.01)

(58) Field of Classification Search
CPC ........ A61D 7/00; A61B 90/36; B64C 39/024; B64C 2201/12
See application file for complete search history.

(56) References Cited

U.S. PATENT DOCUMENTS

| 4,379,440 A   | 4/1983  | Thedford et al. |
| 4,805,341 A   | 2/1989  | Maeda |
| 5,858,357 A   | 1/1999  | Jeannin |
| 6,413,542 B1  | 7/2002  | Etchegaray et al. |
| 8,967,029 B1* | 3/2015  | Calvert ............. F41H 13/00 239/171 |

(Continued)

FOREIGN PATENT DOCUMENTS

| CN | 103995534 A  * | 8/2014 |
| WO | WO 99/66798 A1 | 12/1999 |

OTHER PUBLICATIONS

Translation of Chinese Patent No. 103995534A to Chen from google patents (https://www.google.com/patents/CN103995534B?cl=en&dq=103995534&hl=en&sa=X&ved=0ahUKEwiatJXTidbSAhUKTSYKHWIOC-gQ6AEIGjAA)(Mar. 14, 2017).*

(Continued)

*Primary Examiner* — Jean Paul Cass
(74) *Attorney, Agent, or Firm* — Louis J. Percello; Otterstedt, Ellenbogen & Kammer, LLP

(57) ABSTRACT

Parasites are detected and ameliorative actions taken using unmanned aerial vehicles equipped with sensors and equipment for dispensing treatment materials. Physical characteristic data obtained by the sensors is supplemented using a risk management module that increases the confidence level that the diagnosis of a particular parasite on an animal is correct. The risk management module may further be used to assess additional factors, such as the potential harm in applying a selected treatment, in the decision of whether or not to take ameliorative action.

16 Claims, 3 Drawing Sheets

(56) References Cited

U.S. PATENT DOCUMENTS

| | | | | |
|---|---|---|---|---|
| 2003/0226519 A1* | 12/2003 | Burridge | .............. | A01K 13/003 |
| | | | | 119/652 |
| 2004/0198704 A1 | 10/2004 | Shuster et al. | | |
| 2010/0246970 A1* | 9/2010 | Springer | .............. | A01K 11/006 |
| | | | | 382/195 |
| 2011/0273300 A1* | 11/2011 | Brommer | ........... | G06K 19/0723 |
| | | | | 340/573.3 |
| 2012/0053231 A1* | 3/2012 | Paldi | ....................... | A61K 31/00 |
| | | | | 514/44 A |
| 2014/0025233 A1* | 1/2014 | Levien | ..................... | G05D 1/00 |
| | | | | 701/3 |
| 2015/0234387 A1* | 8/2015 | Mullan | .................. | G05D 1/104 |
| | | | | 701/3 |
| 2016/0069743 A1* | 3/2016 | McQuilkin | ........... | G01J 3/2803 |
| | | | | 356/416 |
| 2016/0144734 A1* | 5/2016 | Wang | .................. | B60L 11/1822 |
| | | | | 701/17 |
| 2017/0029099 A1* | 2/2017 | Chen | ........................ | B64C 27/08 |
| 2017/0042102 A1* | 2/2017 | Safreno | .................. | A01H 1/025 |

OTHER PUBLICATIONS

Pedretti, Joe, Controlling External Parasites on the Organic Farm, Organic Valley, pp. 1-2, Dec. 2014, Downloaded From http://www.kingsagriseeds.com/blog/wp-content/uploads/2014/12/controlling_parasites-on-the-organic-Farm.pdf.

* cited by examiner

US 9,943,387 B2

UNMANNED AERIAL VEHICLE-BASED SYSTEM FOR LIVESTOCK PARASITE AMELIORATION

FIELD

The present disclosure relates to the detection and management of parasites afflicting animals using unmanned aerial vehicles (UAVs).

BACKGROUND

Unmanned aerial vehicles have been developed for a number of uses, including surveillance, aerial filming, agricultural applications, and recreation. They are commonly referred to as drones. UAV designs include fuselage/wing assemblies resembling planes as well as helicopter and quadcopter configurations. Sensors such as gyroscopes, accelerometers, altimeters, GPS modules, cameras and/or payload monitors may be incorporated within UAVs. Gimbals may be used to mount cameras in UAVs. Radio signals generated by a transmitter/receiver, a smartphone, a tablet or other device can be used to control a UAV. UAVs can operate partially or completely autonomously. Functions such as hovering and returning to home can, for example, be provided autonomously. Data obtained by UAVs can be stored onboard using, for example, SD cards, or transmitted wirelessly. UAVs have been employed in the agriculture industry for purposes such as monitoring livestock and crops as well as crop dusting.

Common external parasites afflicting cows and some other livestock include lice, mange, and ticks. Five species of lice often affect cattle in the U.S. One species is a biting or chewing louse; the other four are sucking lice. There are two species of mange mites that most often affect cattle. *Chorioptes bovis* is a mange mite that infests cattle and is commonly known as "tailhead mange." It is the most common type of mange found in the U.S. It is a problem primarily in winter in all types of cattle, but especially in dairy cattle which are housed in closed quarters. *Sarcoptes scabiei* var. *bovis* is a burrowing mite that infests cattle and is frequently referred to as "neck and tail mange," although it may be found on any part of the body. Ticks are mostly a nuisance pest, but under certain conditions can reach numbers capable of affecting the animal. Ticks prefer the ears and neck areas of cattle, which are spots where it is difficult for the animal to remove them. Fortunately, ticks have a complex life cycle and it is not possible for them to breed and reproduce on the animals. The effects of such external parasites are varied. Lice bring about itching and skin irritations, causing animals to scratch, rub, and bite infested areas. Mange also causes skin irritation and itching, with more severe cases resulting in thickened skin, hair loss, and lesions. Ticks cause mostly minor irritation. Economic losses can result from parasite infestations due to irritation, blood loss, depressed appetite, and decreased rate of gain. Mange can affect the mammary gland and interfere with milking. Lactating animals will lose production depending on the level of infestation. Dairy farmers typically take care of the entire parasite problem in one step by using a pour-on pesticide like ivermectin. Organic farmers address common parasite infestations through a combination of prevention and control. Various treatment options are available for controlling parasites, including liquid enzymes that break down exoskeletons of insects/mites, diatomaceous earth, garlic powder, soap, organic plant oils such as soy and canola, and other antiparisitic compounds and solutions.

SUMMARY

Embodiments of the present disclosure provide a means for detecting or inferring the presence of one or more parasites using an unmanned aerial vehicle and using a risk management module that assesses contributing factors that may affect the chances of parasitic attacks on livestock and/or the potential harm that a particular detected parasite may cause.

A method for addressing potential parasite infestations is provided that includes obtaining a first unmanned aerial vehicle (UAV) including one or more sensors for detecting physical characteristics of an animal and/or parasites afflicting the animal. The UAV is launched and located in proximity to an animal. Physical characteristic data is obtained by sensing one or more physical characteristics of the animal and/or a parasite using the one or more sensors. A risk management module configured for assessing a plurality of factors that contribute to parasite infestation of animals is accessed. The plurality of factors that contribute to parasite infestation are assessed using the risk management module in combination with the physical characteristic data to identify a particular parasite. Based on the assessed plurality of factors and the physical characteristic data, an ameliorative action addressing a parasitic infection of the animal by the particular parasite is administered by one or more unmanned aerial vehicles.

Additional aspects of the disclosure are directed to a system for detecting parasites on animals and providing ameliorative action for addressing detected parasites. The system includes a first unmanned aerial vehicle (UAV) including one or more sensors for detecting physical characteristics of an animal and/or parasites afflicting the animal and a risk management module configured for assessing a plurality of factors that contribute to parasite infestation of animals. A processor is configured for processing outputs from the one or more sensors and the risk management module and generating a parasite treatment decision output based on the outputs from the sensors and risk management module. The system further includes one or more unmanned aerial vehicles configured for taking parasite-ameliorating action with respect to the animal.

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1:
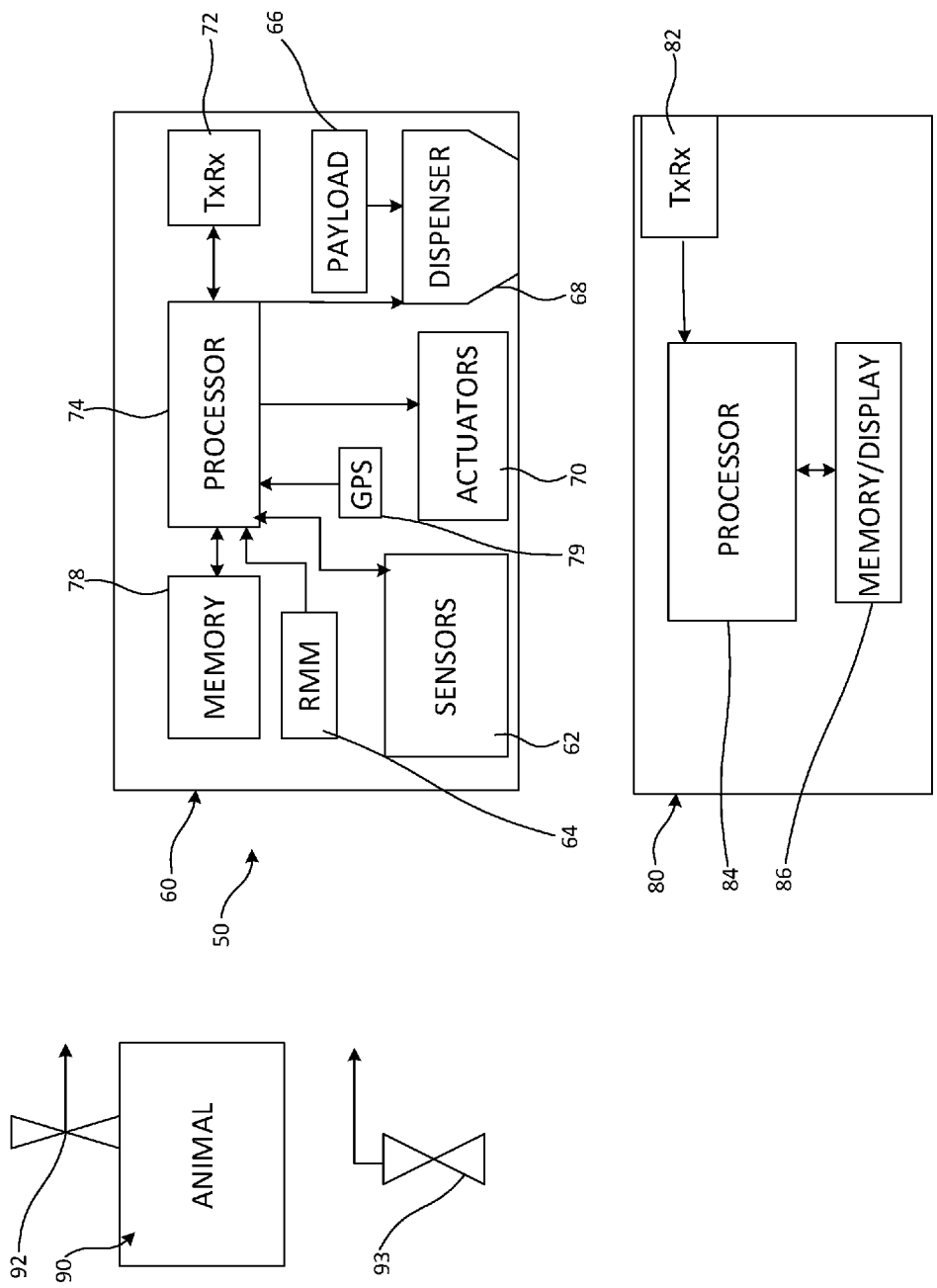
FIG. 1 is a schematic diagram of a system for detecting the presence of parasites and treating detected parasites using an unmanned aerial vehicle.

The subject matter of the instant application will be described with reference to illustrative embodiments. For this reason, numerous modifications can be made to these embodiments and the results will still come within the scope of the invention. No limitations with respect to the specific embodiments described herein are intended or should be inferred.

A system 50 is disclosed herein that includes an unmanned aerial vehicle (UAV) 60 including one or more sensors 62 for detecting or inferring the presence of an external parasite on an animal (e.g. a cow, elephant or a giraffe), and a risk management module (RMM) 64 that assesses contributing factors for external parasites. The UAV in some embodiments further includes a payload 66 including materials for treating an animal and a delivery device (dispenser 68) such as a spray nozzle for applying the materials to the animal. Based on the detection or inference of the presence of an external parasite and input from the risk management module 64, the UAV takes amelioration action with respect to the parasite. Actuators 70 within the UAV control functions such as the dispensing of materials from the payload 66 by the dispenser 68. The actuators further control other operations of the UAV, such as speed controllers and other mechanisms affecting flight.

A system as described above includes one or more UAVs. At least one of the UAVs is configured for detecting or inferring the presence of parasites on the livestock to be monitored. The detection may be based on visual identification using deep neural nets. Visual identification can be assisted by a wireless transmitter/receiver Tx/Rx 72 from the UAV to a remote observer (e.g. farmer or veterinarian) and/or stored in a memory 78 within the UAV for later analysis. In such a manner, a high-definition video feed can be provided to a remote professional. In some embodiments, the UAV includes an internal processor 74 that facilitates determination of whether one or more parasites are present. In other embodiments, such processing is conducted at a remote location. Neural nets can, for example, be used to help identify parasites based on body shape and color. Data obtained by the UAV may be reported to an epidemiology module used for tackling spread of such problems.

The UAV may include geolocation features such as tracking hardware and software 79 that enable, for example, GPS tracking so that each cow (or other animal) can be mapped and the degree of infestation logged. Recorded GPS data can be stored in the memory 78 and/or transmitted by the wireless transmitter/receiver Tx/Rx 72 to a central location. Based on intensity of infestation, appropriate type(s) and amount(s) of anti-parasitic materials to be administered can be determined as described further below, thereby minimizing over-application of such materials and reoccurrence of infestation. In some embodiments, the UAV can identify individual animals using a unique identification that may present on the animal body (e.g. barcode, color pattern, special mark given by the owner, or DNA in the feature). Individual animals provided with RFID tags allows them to be identified, tracked and monitored through time by the UAV-based system.

The UAV is controlled, at least in part, by a device 80 including a transmitter/receiver 82. The device 80 can be a laptop computer, a smartphone, a tablet, or other suitable device. In addition to the transmitter/receiver 82, the device includes a processor 84 and a memory/display 84. Applications for controlling UAVs using such devices are known to the art. One or both of the device 80 and UAV 60 may include a GPS logger. Time is preferably correlated with GPS log data. It will be appreciated that the system 50 can be employed in conjunction with cloud-based systems that receive, maintain and process information obtained by the UAV.

The sensors 62 incorporated within the UAV 60 include one or more cameras for obtaining high-definition digital images, acoustic detector(s) such as piezoelectric sensors, and/or chemical detector(s). High-definition visual images can facilitate decision-making by veterinarians as parasites are often difficult to detect by human eyes. Analysis of digital images can alternatively or additionally be conducted electronically. Acoustic detection facilitates detection of parasites such as flies, though other insects that generate sounds attributable to movement and/or feeding could also be detected. For example, such detection may include the buzz or hum of flies on or around cattle. This may involve audio or vibration sensors on the UAV, on the collars of animals, and/or located in a field where the animal is grazing. For example, analog signals detected by an acoustic detector can be amplified and processed to obtain digital signals that are stored in the memory 78 for later analysis or compared to a reference insect sound spectra stored in the memory for determination of a likely insect species. The patterns obtained are compared to reference patterns to identify/differentiate insect species. Combinations of visual, audio and/or other types of data (e.g. temperature, chemical) can be employed to increase the detection confidence level. The assessment may further include detecting the body temperature of the anima and/or inspecting bleeding spots, evidence of bacteria, or infection formation. Based on said assessment and risk management factor(s) discussed below, the UAV 60 takes amelioration action such as alerting the owner and/or a nearby veterinarian about the current state of the animal for further medication or attention, introducing medication to the animal, and/or applying topical treatment(s) that benefit the animal or address the parasite. Such action may additionally or alternatively be taken by other UAVs configured for treating animals for the diagnosed infections. FIG. 1 includes a diagram showing an exemplary system.

Figure 2:
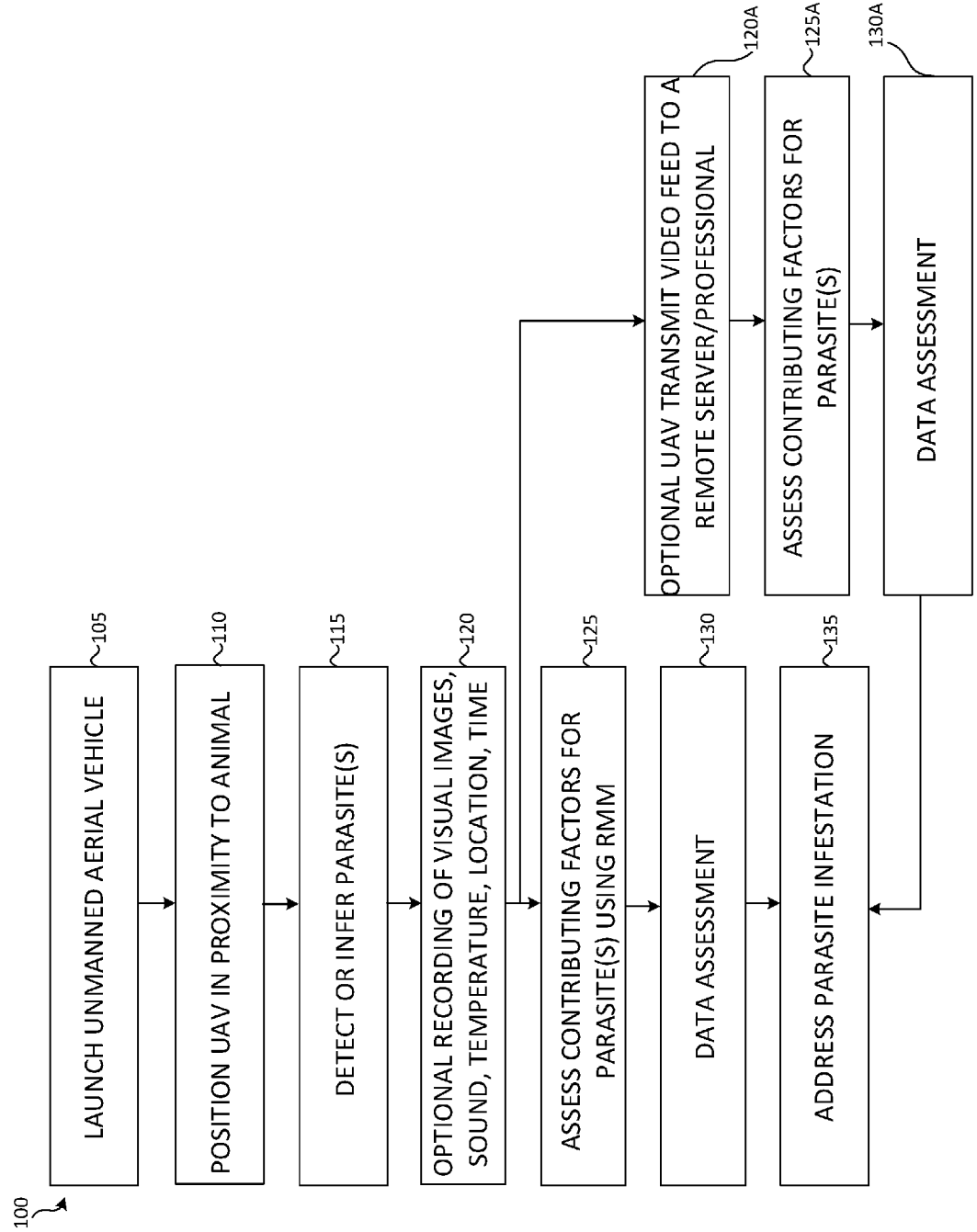
FIG. 2 shows a method for detecting an external parasite and taking ameliatory action responsive to such detection in accordance with an illustrative embodiment.

Referring to FIG. 2, a flow diagram 100 includes exemplary steps for employing a UAV in determining whether ameliorative action is warranted. The UAV is launched in step 105 under the control of an operator. As discussed above, UAVs can be controlled using smartphones or other devices capable of wirelessly communicating with UAVs. As known in the art, the UAV can be controlled manually and/or autonomously, depending on the function to be performed. In some embodiments, the drone is provided with location information and autonomously flies to the location. The UAV is positioned in proximity to an animal in step 110. It may hover near the animal and/or land on the animal. An individual animal is selected in some embodiments of the process by use of a unique identification such as a bar code, color pattern, RFID tag signal, or other indicia that is electronically detected by the UAV. Large animals are often accustomed to having birds land on them and tolerate them to some extent. Animals can also be conditioned to tolerate objects. For example, UAVs carrying payloads of particularly desirable food could be directed to the animals to be analyzed prior to sending UAVs for detecting or treating parasites. Step 115 involves the detection and/or inference of parasites by the UAV. The word "detection" as used herein shall include both direct detection of parasites, for example by obtaining visual images of them, as well as obtaining data from which their presence can be inferred, for example thickened skin, hair loss, lack of appetite, observed lethargy, rubbing against trees or fences, body temperature and/or lesions. Neural networks can, for example, be used to help identify parasites based on detected body shape and color. Parasite diagnosis can be enhanced using, for example, acoustic data and/or thermal data obtained by the UAV and/or sensor(s) 92 worn by the animal 90. In some embodiments, data signals obtained from sensor(s) 93 located in a field or range supplement the data obtained from the UAV sensor(s) 62 and/or the animal-worn sensor(s). Step 120 includes the optional recording of visual images, sound, temperature, location, time, and/or the particular animal targeted by the UAV. Such data can be stored in the memory 78 of the UAV and/or a remote memory 86.

Risk management techniques are employed in conjunction with data obtained using the UAV sensors in determining: 1) whether ameliorative actions should be taken, and 2) the type(s) of ameliorative action(s) to be taken. Risk management, which is not based on data obtained from the UAV sensors, is used to increase the confidence level of parasite detection and the potential value of ameliorative action. Such action entails at least a financial cost and possibly some risk to the animal itself, so a high confidence level is desired to ensure the anticipated benefits will exceed the likely drawbacks. The over-application of anti-parasitic actions can also be reduced or avoided by the application of risk factors to the decision made by a rancher or veterinarian. In some embodiments, the application of artificial neural networks to image data obtained using the UAV sensor(s) allows a particular parasite to be identified. A confidence score is assigned that it is indeed the particular parasite. Acoustical and/or thermal data can also be processed using an artificial neural network that either boosts or lowers the confidence score obtained from using only image data. The confidence score obtained using such data is enhanced through the inclusion of risk management factors in the decision-making process. Analytics based on risk, the type of parasite, and the type of treatment facilitate effective use of resources and livestock management.

Figure 3:
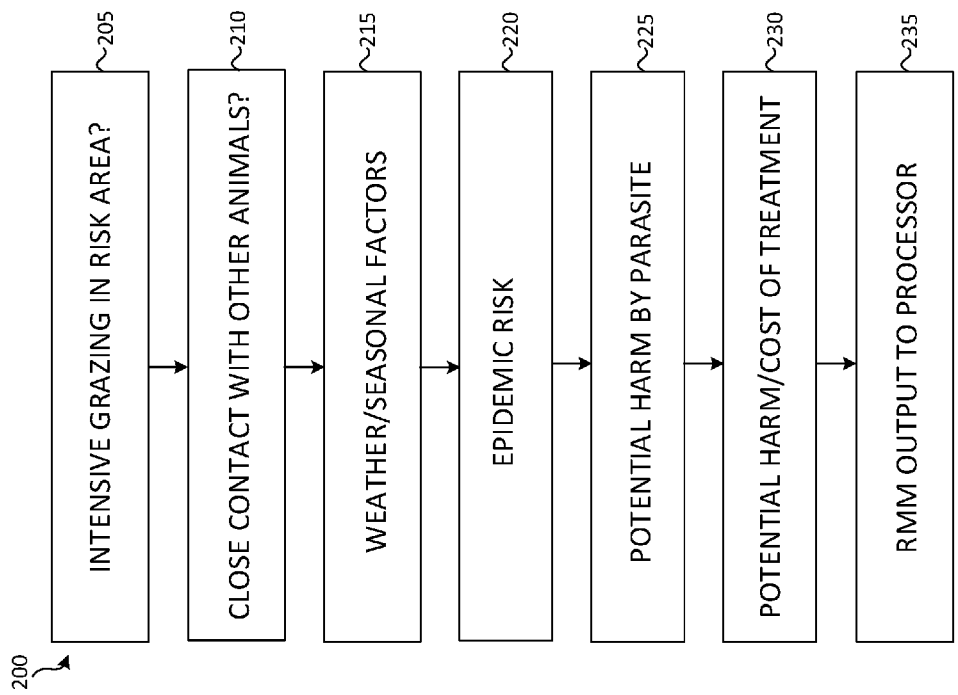
FIG. 3 is a flow diagram showing operation of an exemplary risk management module.

Step 125, which assesses contributing factors relating to the presence or absence of particular parasites and the cost/benefit of treatment, can be further understood by reference to FIG. 3. This figure is a flow diagram 200 showing processing performed by an exemplary risk management module (RMM) 64. A series of factors that contribute to enhancing the confidence level that trigger a decision to act is assessed by the module. Some of the factors relate to the confidence level of the diagnosis of a parasite based on sensor output while others relate to the cost/benefit of treatment. Assessment of the grazing habits of the livestock, if known, is a step 205 in the exemplary sequence. Intensive grazing in woodland areas, for example, increases the likelihood of a tick infestation. In one hypothetical situation, ticks have been detected using sensor information and, based on deep neural nets, assigned an eighty percent (80%) confidence score. If the overall risk of a tick infestation is high based on woodland grazing, the confidence in the UAV sensor-based diagnosis is raised and the rancher would be more likely to take ameliorative action. A second step 210 assesses whether livestock have been in close contact with each other, such as when they have been confined in a limited area. Situations that lead to frequent contact among livestock contribute to the spread of parasites and raise the confidence level of a sensor-based parasite diagnosis. Steps 205 and 210 both relate to the presence of animals in risk areas. Some areas may create greater risks with respect to certain types of parasites than other risk areas. Weather (including seasonal factors and weather forecasts) can also play an important role, and is assessed in step 215. Some weather/seasons are conducive to the spread of certain species of parasites while others would tend to negate an otherwise positive diagnosis based on the UAV sensors and/or other sensors that may be carried by the livestock. For example, *Chorioptes bovis* is a mange mite that infests cattle and is commonly known as "tailhead mange" as it is often found at the base of the tail. It is found primarily in the autumn and winter when cattle are more likely to be confined. If lesions are captured in digital images obtained by the UAV, for example, in the legs and/or base of the tail (but not most other areas) that infer the presence of such mites, and the animals are in close contact (step 210) and it is winter (step 215), the confidence of the mite diagnosis based originally on the visual images is enhanced by the risk management module. This does not necessarily mean that ameliorative action will be taken as there are additional factors to be assessed using the RMM, but higher confidence in the sensor-based diagnosis is important in the ultimate decision as to whether to take such action. Sensors located within a field or range, such as sensor 93 in FIG. 1, may be employed to obtain weather-related information to be used in risk assessment as part of step 215. The sensor may include, for example, a thermometer, barometer, rain gauge, and/or other devices for obtaining such risk management input. Step 220 involves an assessment of epidemic risk. For example, the risk management module may make use of a web crawler to obtain information from news sites and livestock-related sites that may suggest a pending or likely epidemic. Past parasite infestation patterns may be included within step 220 to predict the likelihood of infestation of a given herd. The risk for an entire herd of livestock is evaluated in such a manner and factors into the decisions regarding possible amelioration of a single animal and/or a herd. Step 225 is an exemplary step that does not relate to the confidence level of the parasite diagnosis, but rather the decision as to whether amelioratory step(s) are to be taken. In other words, step 225 relates to the confidence level of selecting a treatment. For example, if the potential harm to livestock by a diagnosed parasite is likely to be low, the rancher may choose against amelioratory treatments despite a high confidence level in the parasite diagnosis. Step 230 is a further exemplary step that relates to decision-making as opposed to parasite diagnosis. The administration of some ameliorative treatments may cause unwanted side effects, thereby weighing against a possible decision to treat an animal. The cost of treatment may also be assessed as the rancher needs to carefully allocate resources in operating a ranch or rangeland. Following assessment of the applicable risk factors, the risk management module (RMM) 64 provides an output in step 235 to a processor which assesses the output of the RMM in combination with the output relating to parasite diagnosis. It will be appreciated that the RMM may include more than one module.

In some embodiments, the processing of sensor information using, for example, a deep neural network, results in the assignment of a confidence score that a given parasite is present. This confidence score is adjusted either up or down using the RMM. The decision to provide amelioratory treatment (step 135) is based on the adjusted confidence score in some embodiments. The UAV, for example, may be programmed by a rancher or a veterinarian to automatically and safely apply a spray to an animal should the adjusted confidence score be at least at a given level for a given parasite. The adjusted confidence score may alternatively be employed in conjunction with an actual assessment of the sensed parameters by the rancher or veterinarian. Step 130 involves data assessment and decision-making based on the adjusted confidence score, which takes into account information obtained by the UAV sensor(s), possibly sensor(s) worn by the animal 90, as well as the factors included in the RMM. One of the processors 74, 84 is configured to make such an assessment in the exemplary system 50 shown in FIG. 1. The assessment may be supplemented by review of some or all data by a rancher or veterinarian.

Ameliorative action taken by the UAV 60 can be in a variety of forms, including the physical removal of parasites and the application of materials that repel, kill or impair parasite functions. In some embodiments, the actuators 70 include a nozzle for delivering safe substances to an animal for treating parasites. The UAV may apply, for example, a liquid enzyme spray that breaks down the exoskeleton of an insect or mite. Such liquid enzymes are known in the art. Alternatively, an oil such as safflower oil or canola oil may be dispensed along the back of an animal. Organic plant oils operate by clogging pores of targeted parasites. Macerated garlic carried by the oil is suitable for worm infestations and lice in cattle, sheep and horses. Neem oil and pyrethrin are further exemplary materials to be applied by the UAV in response to detection of some parasites. Soap may be applied by the UAV in some embodiments to kill lice and mites, it being appreciated that repeat treatments will likely be necessary. The UAV may be further configured to deposit solid materials such as powders to address a parasite infestation. Diatomaceous earth is not chemically active but kills insects and mites by piercing their exoskeletons. Garlic powder is a further alternative. Pneumatic dispensers and various types of spray guns for dispensing liquid and powder pesticides are known to the art and comprise the dispenser 68 in some embodiments. Some types of dispensers dispensed charged particles to promote particle adherence. U.S. Pat. No. 4,805,341, which is incorporated by reference herein, discloses an exemplary powder dispenser that may be incorporated within the UAV with a pressurized air source to facilitate distribution of the powder. The UAV may be further adapted to affix rings such as ear rings that discourage parasites such as ticks. In some embodiments, the payload 66 of the UAV includes an anti-parisitic compound that can be poured on the back of an animal. The actuators 70 could then include a valve (not shown) that is electronically operated for releasing the pour-on material from the payload for a selected duration. An exemplary pour-on compound is disclosed in U.S. Pat. No. 6,413,542, which is incorporated by reference herein. Canola or safflower oil including macerated garlic is another pour-on substance that is included in the payload 66 in some embodiments. Mechanical devices such as tweezers or brushes can be employed by the UAV in some embodiments to physically remove parasites.

In some embodiments, cattle are provided with RFID tags to allow individual animals to be identified, tracked and monitored over time by one or more UAVs. Identification tags include parasite-detecting sensor(s) 92 in some embodiments. Such sensors 92 capture visual images, acoustic data, thermal data, and/or parasites themselves in some embodiments. For example, an ear tag may include a trap for collecting parasites such as ticks and a camera for transmitting visual images of the trap contents. If ticks are detected on some of the tracked cattle 90 using such sensors 92, this data in combination with possible contributing factors assessed by the risk management module, is used to dispatch one or more UAVs to address the parasites. RFID transmissions allow the UAVs to locate the infected animals and treat them and/or gather further data usable in the diagnosis of parasites. It will be appreciated that, in some embodiments, a first UAV is used to obtain data relating to the physical characteristics of an animal while a second UAV is used to take ameliorative action with respect to the animal based on such physical data and contributory risk factors. A smaller, lighter UAV may accordingly be used to obtain visual images and/or sound data that are less likely to disturb the animal, even if they lands on the animal. Larger, heavier UAVs carrying payloads of parasite treatment materials would then be used to treat the animal without necessarily landing on it.

The UAV may or may not include processing capability for processing the data obtained by the onboard sensors 62 and/or other sensors such as those worn on collars or placed in the field. Referring again to FIG. 2 and step 120A, the UAV optionally transmits video data to a remote server and/or a professional for such processing. Other data, such as acoustical data and temperature data, whether obtained by the UAV or elsewhere, can also be transmitted in step 120A. Contributing factors relating to parasitic infection are received in step 125A. Exemplary contributing factors are discussed above with respect to step 125. The transmitted sensory data and the contributing factors are assessed in step 130A, which corresponds to step 130 discussed above. If the data assessment results in an output supporting amelioration, a signal is transmitted to the UAV and step 135 is performed by the UAV.

In some embodiments, a single UAV is configured to perform both parasite detection and amelioration. Alternatively, a second drone could be triggered for the amelioration. A UAV that performs both functions could, in real-time, detect and then quickly help the animal. There would accordingly be very little delay between detection and help for the animal. A UAV that performs both functions (parasite detection and amelioration) can be further configured to, at times, transmit a signal to a second UAV if the first does not currently carry the appropriate treatment (e.g. anti-parasite solution) and/or does not have the appropriate applicator (e.g. banding nozzles for targeted spraying, solid stream nozzles for concentrated paths at high speeds, misting nozzles). Step 135 could accordingly be performed by a complementary UAV receiving a signal from the parasite-sensing UAV.

Given the discussion thus far and with reference to the exemplary embodiments discussed above and the drawings, it will be appreciated that, in general terms, an exemplary method for addressing potential parasite infestations includes obtaining a first unmanned aerial vehicle (UAV) 60 including one or more sensors 62 for detecting physical characteristics of an animal and/or parasites afflicting the animal. The first UAV is launched and then located in proximity to an animal. While in proximity to the animal, physical characteristic data relating to the animal and/or a parasite afflicting the animal is obtained by the one or more sensors. For example, a visual sensor such as a digital camera may provide digital images of a parasite while an infrared sensor obtains information relating to the body temperature of the animal and an acoustic sensor detects sounds generated by the animal and/or the parasite. A risk management module 64 is configured for assessing a plurality of factors that contribute to parasite infestation of animals. The plurality of factors that contribute to parasite infestation is assessed in combination with the physical characteristic data to identify a particular parasite. Based on the assessed plurality of factors, for example those identified in the flow diagram 200 discussed above with respect to FIG. 3, and the physical characteristic data, an ameliorative action addressing a parasitic infection of the animal by the particular parasite is administered by one or more unmanned aerial vehicles. In some embodiments, the risk management module is further configured to assess potential harm of one or more parasites to the animal and the decision to take ameliorative action is further based on the potential harm of one or more parasites. In some embodiments, the first unmanned aerial vehicle is caused to take the ameliorative action. The method may further include affixing one or more parasite detectors and associated transmitters to the animal, the transmitter being configured for transmitting signals responsive to input from the one or more parasite detectors, and the launching the first unmanned aerial vehicle and/or other UAV carrying a payload of treatment material is responsive to signals from the transmitter. The animal may be identified using RFID tags or the like. The first UAV may be directed to a particular animal using such identification means. In some embodiments of the method, the first UAV lands on an animal. UAVs having hovering capabilities facilitate landing on an animal.

A system for detecting parasites on animals and providing ameliorative action for addressing detected parasites includes a first unmanned aerial vehicle 60 including one or more sensors 62 for detecting physical characteristics of an animal and/or parasites afflicting the animal. The system further includes a risk management module 64 configured for assessing a plurality of factors that contribute to parasite infestation of animals. A processor (74 or 84) configured for processing outputs from the one or more sensors 62 and the risk management module 64 and generating a parasite treatment decision output based on the outputs from the sensors and risk management module. The system further includes one or more unmanned aerial vehicles 50 configured for dispensing parasite-ameliorating materials on the animal. The one or more UAVs may or may not include the first UAV including the sensors 62. The plurality of factors that contribute to parasite infestation may include animal presence in a risk area (for example in a woodland area) and weather. Veterinary service providers can use this system to offer on-demand services. A farmer or a group of farmers in a community or region can subscribe for all services or selective UAV services. The system may further integrate predictive models based on weather forecasts, past worm or parasite patterns, and cohort analysis on livestock databases. In some embodiments, the system also keeps track of parasite outbreaks in other places/locations globally and predicts the likelihood of occurrence in a given herd.

In another embodiments, the risk assessment obtained using the risk management module, the tracking of animal health, and the amelioration actions taken can be an incentive for the farmer to obtain insurance packages for their animals, allow farmers to receive higher market prices for their animals, or improve farmers' eligibility for loan or credit based on their livestock. These benefits are particularly desirable in countries or regions where livestock are most at risk from parasites. The system provides further potential benefits of reducing animal suffering and reducing over-use of anti-parasitic treatments on ranches and in wildlife preserves. Risks to humans associated with the administration of ameliorative actions to farm animals or animals in wildlife preserves are also reduced. Animals that naturally fear human intervention also benefit from the system as there is no need to capture or anesthetize an animal in order to obtain a diagnosis or provide treatment.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The above-described embodiments are intended to be illustrative only. Other embodiments may, for example, utilize different materials and processing steps from those expressly set forth above to achieve embodiments falling within the scope of the present disclosure. These many alternative embodiments will be apparent to one having ordinary skill in the relevant arts.

All the features disclosed herein may be replaced by alternative features serving the same, equivalent, or similar purposes, unless expressly stated otherwise. Thus, unless expressly stated otherwise, each feature disclosed is one example only of a generic series of equivalents. The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. Terms such as "above" and "below" are used to indicate relative positioning of elements or structures to each other as opposed to relative elevation.

It should also be noted that, in some alternative implementations, the steps of the exemplary methods may occur out of the order noted in the figures. For example, two steps shown in succession may, in fact, be executed substantially concurrently, or certain steps may sometimes be executed in the reverse order, depending upon the functionality involved.

It is to be appreciated that the various layers and/or regions shown in the accompanying figures may not be drawn to scale. Furthermore, one or more semiconductor layers of a type commonly used in such integrated circuit devices or other layers may not be explicitly shown in a given figure for ease of explanation. This does not imply that the semiconductor layer(s) or other layer(s) not explicitly shown are omitted in the actual integrated circuit device.

Any element in a claim that does not explicitly state "means for" performing a specified function or "step for" performing a specified function is not to be interpreted as a "means for" or "step for" clause as specified in AIA 35 U.S.C. § 112(f). In particular, the use of "steps of" in the claims herein is not intended to invoke the provisions of AIA 35 U.S.C. § 112(f).

What is claimed is:

1. A method for addressing potential parasite infestations, comprising:
   obtaining a first unmanned aerial vehicle including one or more sensors for detecting physical characteristics of an animal and/or parasites afflicting the animal;
   launching the first unmanned aerial vehicle;
   locating the first unmanned aerial vehicle in proximity to an animal;
   obtaining physical characteristic data by sensing one or more physical characteristics of the animal and/or a parasite using the one or more sensors;
   accessing a risk management module configured for assessing a plurality of factors that contribute to parasite infestation of animals;
   assessing the plurality of factors that contribute to parasite infestation using the risk management module in combination with the physical characteristic data to identify a particular parasite, and
   based on the assessed plurality of factors and the physical characteristic data, causing an ameliorative action addressing a parasitic infection of the animal by the particular parasite to be administered by one or more unmanned aerial vehicles,
   wherein the one or more sensors include a visual image sensor,
   wherein the risk management module is further configured to assess potential harm of one or more parasites to the animal, and wherein causing the ameliorative action is further based on the potential harm to the animal by the particular parasite, wherein the risk management module is further configured to assess epidemic risk of one or more parasites to the animal, and wherein causing the ameliorative action is further based on the epidemic risk.

2. The method of claim 1, wherein the one or more sensors include an acoustic sensor.

3. The method of claim 1, wherein the plurality of factors include animal presence in a risk area and weather.

4. The method of claim 1, further including causing the first unmanned aerial vehicle to cause the ameliorative action.

5. The method of claim 1, wherein locating the first unmanned aerial vehicle in proximity to an animal further includes landing the first unmanned aerial vehicle on the animal.

6. A method for addressing potential parasite infestations, comprising:
- electronically identifying an animal by an RFID transponder;
- obtaining a first unmanned aerial vehicle including one or more sensors for detecting physical characteristics of the animal and/or parasites afflicting the animal;
- launching the first unmanned aerial vehicle;
- causing the first unmanned aerial vehicle to move into proximity with the animal based on the electronic identification of the animal by the first unmanned aerial vehicle;
- obtaining physical characteristic data by sensing one or more physical characteristics of the animal and/or a parasite using the one or more sensors;
- accessing a risk management module configured for assessing a plurality of factors that contribute to parasite infestation of animals;
- assessing the plurality of factors that contribute to parasite infestation using the risk management module in combination with the physical characteristic data to identify a particular parasite, and
- based on the assessed plurality of factors and the physical characteristic data, causing an ameliorative action addressing a parasitic infection of the animal by the particular parasite to be administered by one or more unmanned aerial vehicles.

7. A method for addressing potential parasite infestations, comprising:
- affixing one or more parasite detectors and a transmitter to an animal, the transmitter being configured for transmitting signals responsive to input from the one or more parasite detectors;
- obtaining a first unmanned aerial vehicle including one or more sensors for detecting physical characteristics of the animal and/or parasites afflicting the animal;
- launching the first unmanned aerial vehicle, wherein launching the first unmanned aerial vehicle is responsive to signals from the transmitter;
- locating the first unmanned aerial vehicle in proximity to the animal;
- obtaining physical characteristic data by sensing one or more physical characteristics of the animal and/or a parasite using the one or more sensors;
- accessing a risk management module configured for assessing a plurality of factors that contribute to parasite infestation of animals;
- assessing the plurality of factors that contribute to parasite infestation using the risk management module in combination with the physical characteristic data to identify a particular parasite, and
- based on the assessed plurality of factors and the physical characteristic data, causing an ameliorative action addressing a parasitic infection of the animal by the particular parasite to be administered by one or more unmanned aerial vehicles.

8. A system for detecting parasites on animals and providing ameliorative action for addressing detected parasites, comprising:
- one or more parasite detectors worn by an animal;
- a transmitter worn by the animal, connected in communication with the parasite detectors, and configured for transmitting signals responsive to input from the one or more parasite detectors;
- a first unmanned aerial vehicle including one or more sensors for detecting physical characteristics of the animal and/or parasites afflicting the animal;
- a risk management module configured for assessing a plurality of factors that contribute to parasite infestation of animals;
- a processor configured for processing outputs from the one or more sensors and the risk management module and generating a parasite treatment decision output based on the outputs from the sensors and risk management module, the processor being configured for processing the signals from the transmitter, launching the first unmanned aerial vehicle in response to the signals from the transmitter, and generating the parasite treatment decision output based in part on the signals from the transmitter, and
- one or more additional unmanned aerial vehicles configured for taking parasite-ameliorating action with respect to the animal.

9. The system of claim 8, wherein the one or more unmanned aerial vehicles are further configured to dispense parasite-ameliorating material in response to the treatment decision output generated by the processor.

10. The system of claim 9, wherein the one or more unmanned aerial vehicles include the first unmanned aerial vehicle.

11. The system of claim 10, wherein the one or more sensors include a visual sensor for obtaining digital images.

12. The system of claim of claim 8, wherein the plurality of factors include animal presence in a risk area and weather.

13. The system of claim 8, wherein the one or more sensors include a visual sensor for obtaining digital images.

14. The system of claim 13, wherein the risk management module is further configured for assessing potential harm by a diagnosed parasite to the animal and generating the parasite treatment decision output based in part on the assessed potential harm by the diagnosed parasite.

15. The system of claim 13, wherein the processor is further configured to process outputs from the one or more sensors using a neural network configured to identify parasites.

16. The system of claim 8, wherein the first unmanned aerial vehicle includes the risk management module and the processor and is further configured to dispense parasite-ameliorating material in response to the treatment decision output generated by the processor.

* * * * *